United States Patent
Kawai

(10) Patent No.: US 9,459,613 B2
(45) Date of Patent: Oct. 4, 2016

(54) ELECTRIC ENDOSCOPE

(71) Applicant: OLYMPUS CORPORATION, Tokyo (JP)

(72) Inventor: Toshimasa Kawai, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 50 days.

(21) Appl. No.: 14/455,282

(22) Filed: Aug. 8, 2014

(65) Prior Publication Data

US 2015/0054445 A1 Feb. 26, 2015

Related U.S. Application Data

(63) Continuation of application No. PCT/JP2014/052235, filed on Jan. 31, 2014.

(30) Foreign Application Priority Data

Feb. 5, 2013 (JP) ................................. 2013-020746

(51) Int. Cl.
*G05B 11/36* (2006.01)
*G05B 19/404* (2006.01)
(Continued)

(52) U.S. Cl.
CPC ......... *G05B 19/404* (2013.01); *A61B 1/00006* (2013.01); *A61B 1/0016* (2013.01); *A61B 1/00039* (2013.01); *A61B 1/0052* (2013.01); *A61B 1/00055* (2013.01); *A61B 1/0057* (2013.01); *A61B 1/00128* (2013.01); *A61B 1/01* (2013.01); *A61B 1/0002* (2013.01); *A61B 1/0684* (2013.01); *G05B 2219/41078* (2013.01)

(58) Field of Classification Search
CPC ...... G05B 5/01; G05B 19/19; G05B 13/024; H02P 21/06
USPC .................................................. 318/609, 610
See application file for complete search history.

(56) References Cited

U.S. PATENT DOCUMENTS 6,327,493 B1 * 12/2001 Ozawa ................. A61B 5/0073
348/45
7,199,545 B2 * 4/2007 Oleynikov ............. A61B 1/041
104/138.2

(Continued)

FOREIGN PATENT DOCUMENTS

EP      1 972 257 A1      9/2008
EP      2 229 868 A1      9/2010
(Continued)

*Primary Examiner* — Rina Duda
(74) *Attorney, Agent, or Firm* — Scully, Scott, Murphy & Presser, PC

(57) ABSTRACT

An electric endoscope includes a motor that generates a rotational driving force, a torque shaft that transmits the rotational driving force from a proximal end portion to a distal end portion, a connecting section for bending a bending portion by the rotational driving force transmitted by the torque shaft, an input section that instructs a target rotation amount of the motor, a detecting section that detects rotation information of the motor in a rotating state thereof, an estimating section that estimates a rotation state of the motor based on the rotation information, a motor physical model, a torque shaft physical model and a connecting section physical model, and a control section that performs control so that the rotation state of the distal end portion matches with a rotation state of the target rotation amount based on the estimated rotation state of the motor.

9 Claims, 10 Drawing Sheets

(51) Int. Cl.
*A61B 1/005* (2006.01)
*A61B 1/00* (2006.01)
*A61B 1/01* (2006.01)
*A61B 1/06* (2006.01)

(56) References Cited

U.S. PATENT DOCUMENTS

| | | |
|---|---|---|
| 2008/0262306 A1 | 10/2008 | Kawai |
| 2011/0009698 A1* | 1/2011 | Ashida ............... A61B 1/00006 600/118 |
| 2011/0015786 A1 | 1/2011 | Kawai |
| 2011/0065994 A1 | 3/2011 | Kudoh et al. |
| 2011/0137122 A1* | 6/2011 | Kawai .................. A61B 1/0052 600/118 |

FOREIGN PATENT DOCUMENTS

| | | |
|---|---|---|
| EP | 2 394 799 A1 | 12/2011 |
| EP | 2 441 375 A1 | 4/2012 |
| JP | 2007-037564 A | 2/2007 |
| JP | 2007-044074 A | 2/2007 |
| JP | 2007-185355 A | 7/2007 |
| JP | 2010-213969 A | 9/2010 |
| JP | 2013-017785 A | 1/2013 |
| WO | WO 2010/090059 A1 | 8/2010 |
| WO | WO 2010/143715 A1 | 12/2010 |

* cited by examiner

ELECTRIC ENDOSCOPE

CROSS REFERENCE TO RELATED APPLICATION

This application is a continuation application of PCT/JP2014/052235 filed on Jan. 31, 2014 and claims benefit of Japanese Application No. 2013-020746 filed in Japan on Feb. 5, 2013, the entire contents of which are incorporated herein by this reference.

BACKGROUND OF THE INVENTION

1. Field of the Invention

The present invention relates to an electric endoscope provided with a driving section that rotationally drives an object to be driven.

2. Description of the Related Art

In recent years, an endoscope has been broadly used in a medical field and an industrial field. Particularly, in the medical field, an endoscope that is easy for a surgeon to operate when performing treatment or the like for remedy by grasping the endoscope has been desired.

For example, in Japanese Patent Laid-Open Publication No. 2007-37564 as a first conventional example, it is configured that an ultrasound transducer to be rotationally driven is housed in a transducer housing portion provided at a distal end portion of an insertion portion, and the ultrasound transducer is rotationally driven by a motor provided in an operation portion through a flexible shaft inserted through the insertion portion, to thereby enable radial scanning by ultrasound, by the ultrasound transducer. Further, it is disclosed to cope with rotation delay by providing an encoder in the vicinity of a proximal end of the ultrasound transducer and detecting the rotation delay of the flexible shaft by the encoder.

Further, in Japanese Patent Laid-Open Publication No. 2007-44074 as a second conventional example, there is disclosed a configuration in which an ultrasound probe is insertable into a treatment instrument insertion channel of an endoscope, an ultrasound transducer is mounted at a distal end portion of a flexible shaft which is inserted through the ultrasound probe, a rear end of the flexible shaft is connected to a motor unit and the ultrasound transducer is rotationally driven by the motor unit through the flexible shaft. Further, it is disclosed to detect a rotational position of a distal end of the flexible shaft with high precision by an encoder provided at the distal end of the flexible shaft, and obtain a detailed ultrasound tomographic image by radial scanning.

SUMMARY OF THE INVENTION

An electric endoscope according to an aspect of the present invention includes: a motor that generates a rotational driving force; a torque shaft having flexibility, for transmitting the rotational driving force, the torque shaft having a proximal end portion connected to the motor; a mechanical connecting section for bending a bending portion by the rotational driving force transmitted through the torque shaft, the mechanical connecting section being connected to a distal end portion of the torque shaft; an input section that inputs a command value for instructing a target rotation amount of the motor; a detecting section that detects rotation information of the motor in a rotating state thereof; an estimating section that estimates a rotation state of the motor reflecting a rotation state of the distal end portion based on the rotation information, a motor physical model that simulates the motor, a torque shaft physical model that simulates the torque shaft and a mechanical connecting section physical model that simulates the mechanical connecting section; and a control section that controls the motor so that the rotation state of the distal end portion matches with a rotation state of the target rotation amount based on the rotation state of the motor estimated by the estimating section.

DETAILED DESCRIPTION OF THE PREFERRED EMBODIMENTS

Figure 1:
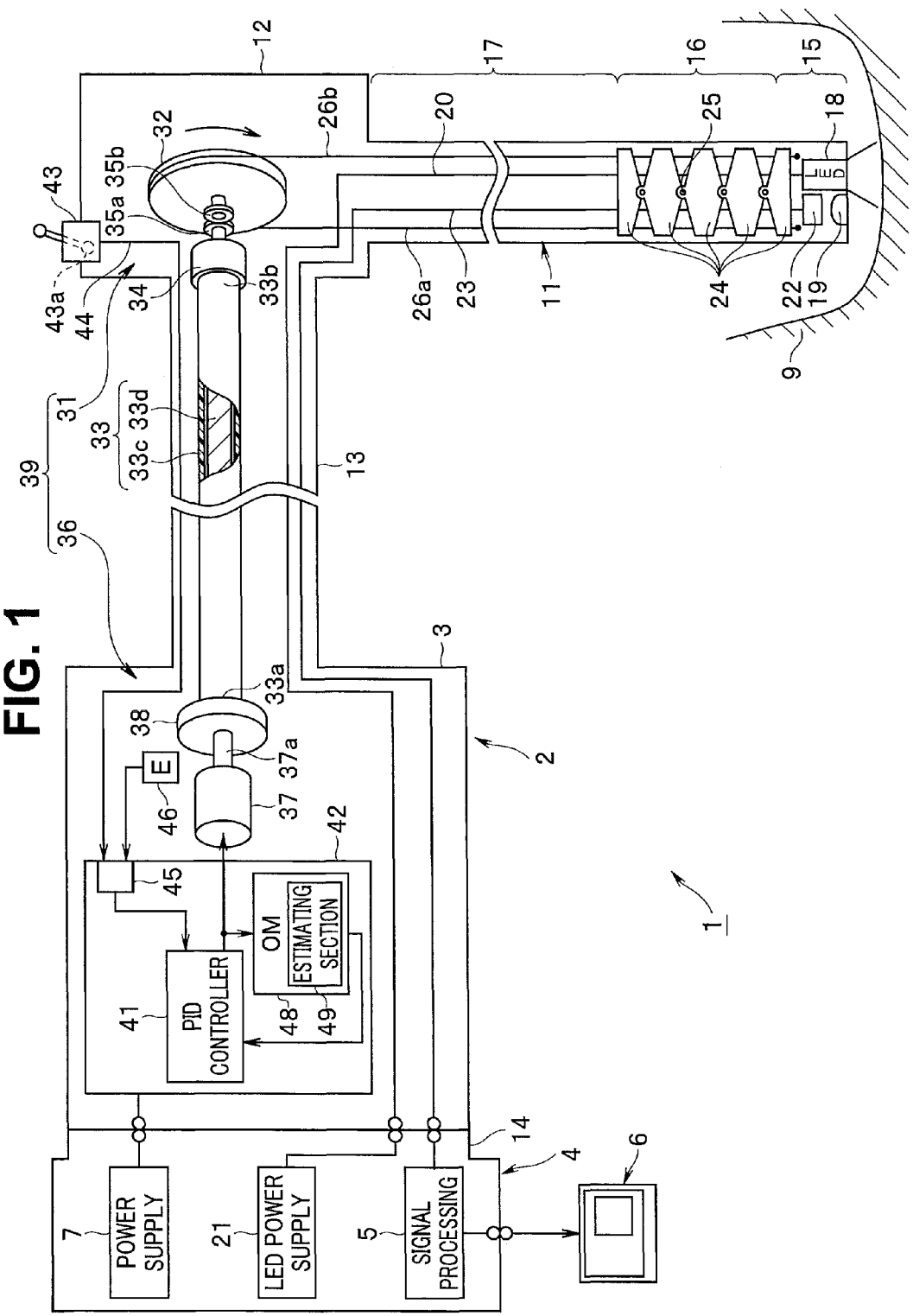
FIG. 1 is a diagram showing an entire configuration of an endoscope apparatus provided with an electric endoscope according to a first embodiment of the present invention.

Hereinafter, embodiments of the present invention will be described referring to the drawings.

First Embodiment

As shown in FIG. 1, an endoscope apparatus 1 with a first embodiment of the present invention is configured by an electric endoscope 2, a signal processing apparatus 4 to which a connector 3 of the electric endoscope 2 is detachably connected, and a monitor 6 to which a standard video signal generated by a signal processing section 5 in the signal processing apparatus 4 is inputted, to thereby display an endoscopic image corresponding to the video signal.

The electric endoscope 2 includes an insertion portion 11, which has flexibility, to be inserted into a body cavity of a subject 9, an operation portion 12 provided at a rear end (a proximal end) of the insertion portion 11 and a universal cable 13 which has flexibility and extends from the operation portion 12, and the connector 3 provided at an end portion of the universal cable 13 is detachably connected to a connector receiver 14 of the signal processing apparatus 4.

The insertion portion 11 includes a distal end portion 15 provided at an distal end of the insertion portion, a bending portion 16 provided at a rear end of the distal end portion 15, and a flexible portion 17 extending from a rear end of the bending portion 16 to a rear end of the insertion portion 11.

An illumination window and an observation window are provided adjacent to each other at the distal end portion 15, a white light emitting diode (white LED) 18 which emits illumination light is mounted at the illumination window, and an objective lens 19 is mounted at the observation window.

The white LED 18 is connected to an LED power supply circuit 21 in the signal processing apparatus 4 via a drive line 20 inserted through the insertion portion 11, etc. of the electric endoscope 2, and generates white illumination light by LED power supply supplied from the LED power supply circuit 21, to illuminate the inside of the body cavity.

An illuminated object such as an affected part forms an optical image by objective lens 19 on an image pickup surface of a charge coupled device (CCD) 22 arranged at an image forming position of the objective lens.

The CCD 22 is connected to a signal processing section 5 in the signal processing apparatus 4 via a signal line 23 inserted through the insertion portion 11, etc. of the electric endoscope 2, and outputs an image pickup signal obtained by photoelectric conversion by application of a drive signal by a drive circuit, not shown, in the signal processing section 5. A signal processing circuit, not shown, in the signal processing section 5 generates a standard video signal for display on the monitor 6 from the inputted image pickup signal, and outputs the signal to the monitor 6. On a display surface of the monitor 6, an image of the object picked up by the CCD 22 is displayed as the endoscopic image. It is noted that the signal processing apparatus 4 includes a power supply circuit 7 which, when the connector 3 is attached, provides power supply for operation to a motor controller 42, as described later, arranged in the connector 3.

The bending portion 16 includes a plurality of circular ring-shaped bending pieces 24 and the bending pieces 24 adjacent to each other in a longitudinal direction of the bending portion 16 are rotatably connected through rivets arranged at positions in an up-and-down direction, for example. It is noted that, in FIG. 1, a direction perpendicular to the paper surface is defined as the up-and-down direction (in which the bending portion 16 is bent), and a horizontal direction within the paper surface is defined as a right-and-left direction.

Further, bending wires 26a and 26b as a pair are inserted through the insertion portion 11 along inner walls in the right-and-left direction, one end of each of the bending wires 26a and 26b, which constitute a pulling mechanism for bending the bending portion 16 by pulling, is fixed to the distal end portion 15 and the other end of each of the bending wires 26a and 26b is wound on a sprocket (or a pulley) 32 which constitutes a mechanical connecting section or a mechanical coupling section (abbreviated as "mecha-coupling section") 31.

Besides, in FIG. 1, the configuration in which the bending portion 16 is bent in the right-and-left direction (by connecting the bending pieces 24 of the bending portion 16 to be rotatable by the rivets 25 arranged in the up-and-down direction) is shown, but it may be configured such that the bending pieces 24 are connected to be rotatable in the right-and-left direction also and bending wires in a pair are provided along the inner walls in the up-and-down direction in the insertion portion 11. Then, by further winding a proximal end of each of the pair of the bending wires on (a sprocket of) a mechanical coupling section which is separate from the mechanical coupling section 31, a structure in which bending in the up-and-down direction is allowed in addition to the bending in the right-and-left direction can be constructed. In this case, two potentiometers for detecting tilting directions, etc. of a joystick 43, as described later, may be provided for detection in the up-and-down direction in addition to the right-and-left direction.

The mechanical coupling section 31 comprises a joint 34 connected to a torque shaft 33 which is provided at a proximal end of the mechanical coupling section 31, a gear 35a connected to the joint 34, a gear 35b connected to the sprocket 32 (and meshed with the gear 35a), and the sprocket 32.

A proximal end of the mechanical coupling section 31 is connected to a geared motor 36, which is arranged in the connector 3 and constitutes an electric driving section, via the torque shaft 33 having flexibility which is inserted through the universal cable 13 and serves as a transmission member of a driving force.

The geared motor 36 comprises a motor 37 and a gear 38 connected to a rotating shaft 37a of the motor 37. Hereinafter, the geared motor 36 is simply referred to as "motor 36" and the motor 37 is referred to as "motor main body 37".

A proximal end portion 33a of the torque shaft 33 is connected to a rotating shaft 34a of the motor 36, and the torque shaft 33 transmits a rotational driving force (torque) of the motor 36, to which the proximal end portion 33a of the torque shaft 33 is connected, to a distal end portion 33b, to rotate the sprocket 32 of the mechanical coupling section 31 which is connected to the distal end portion 33b.

That is, the torque shaft 33 forms a transmission member that has a driving axis with the proximal end portion 33a connected to the rotating shaft 34a of the motor 36 which constitutes the driving section, and the distal end portion 33b connected to the mechanical coupling section 31 as an object to be driven, rotates around the driving axis, and transmits the rotational driving force from the driving section to the object to be driven.

The torque shaft 33 is, as shown in FIG. 1, comprises an external tube 33c having flexibility, a flexible closely wound coil (or closely wound spiral) 33d which is arranged inside the external tube and transmits the rotational driving force. A longitudinal direction of the closely wound coil 33d forms the driving axis. It is noted that the closely wound coil 33d may be defined as the torque shaft 33.

Further, by rotating the sprocket 32 via the torque shaft 33 in a direction shown by the arrow, for example, one of the pair of the bending wires 26a and 26b (in this case, the bending wire 26b) is pulled and the other is slackened, so that the bending portion 16 can be bent to a side of the pulled bending wire 26b. By rotating the sprocket 32 in the opposite direction, the bending portion 16 can be bent to a side of the bending wire 26a.

An electric bending drive section 39 that bends the bending portion 16 via the pulling mechanism is constituted by the motor 36, the torque shaft 33 and the mechanical coupling section 31.

Further, in the connector 3, there is arranged a motor controller 42 provided with a PID controller (PID-control controller) 41 for performing motion for rotationally driving (the motor main body 37 of) the motor 36 by PID control. Besides, specifically, a configuration shown in FIG. 7 may be used as the PID controller. However, in the present embodiment, there is not provided a function of performing variable control of a gain in a block 93 by inputting a motor-torque estimated value Pt into the PID controller 41 in FIG. 7. Therefore, it is configured that the gain in the block 93 is fixed in the PID controller 41 of FIG. 7. That is, a command value from a command setting section 45, and position information from an observer model 48 are inputted into a block 91 of sum and the block 91 subtracts the latter from the former and output the result to a PID controller main body 92.

The PID controller main body 92 includes the block 93 of a variable gain for performing proportional control, a block 94a of an integral operation of 1/s for performing integral control and a block 94b of a gain Ki which is provided in series with the block 94a, a block 95a of a time-differential operation for performing differential control and a block 95b which is provided in series with the block 95a. These three output values are added up by a block 96 of sum and the result is outputted from an output terminal CMD to the motor 36 of the electric bending drive section 39 and the observer model 48.

Further, in the operation portion 12, there is provided the joystick 43 which forms an input section for performing an instruction input of a bending command value (also referred to simply as "command value") when a user causes the bending portion 16 to bend by a tilting operation of a stick. At a proximal end of the joystick 43, there is provided a potentiometer 43a, for example, which detects a tilting direction and a tilting operation amount (in the right-and-left direction), and the potentiometer 43a outputs a signal, as the bending command value, corresponding to the tilting direction and the tiling operation amount to the command setting section 45 of the motor controller 42 through a signal line 44 in the universal cable 13.

Further, at the motor 36, a motor encoder 46 as a detection section that detects a rotational angle of the rotating shaft 37a of the motor main body 37 (or the gear 38), and the motor encoder 46 detects information of the rotational angle in a rotating state of the motor 36 as rotational information and outputs the detected rotational information to the command setting section 45.

The command setting section 45 outputs a value obtained by subtracting a present rotational angle (rotational position) of the motor 36 detected by the motor encoder 46 from a value obtained by converting the bending command value, which is detected by the potentiometer 43a, into a corresponding rotation target value of the motor 36, to the PID controller 41 to be set as a rotation command value as a provisional target rotation amount.

The PID controller 41 performs the PID control by applying a voltage value as a driving command value for rotationally driving the motor 36 which constitutes the driving section, from the rotation command value inputted from the command setting section 45. That is, the command setting section 45 inputs the rotation command value as the provisional target rotation amount for the driving section into the PID controller 41. In other words, a reference input terminal Ref (see FIG. 3) of the PID controller 41, to which the rotation command value from the command setting section 45 is inputted, constitutes a provisional input section which instructs the provisional target rotation amount (at present point in time) in comparison with the input section which instructs the target rotation amount. In the provisional input section, the rotation command value varies in accordance with a present value of the rotational angle of the motor 36 detected by the motor encoder 46 which constitutes the detection section. By contrast, the input section constituted by the joystick sets a command value as the target rotation amount of the motor 36 which is instructed by the user. Further, the motor controller 42 which constitutes the control section changes the provisional desired rotation amount in accordance with a rotation state of the motor 36 to control the motor 36 to match with the target rotation amount.

Further, the motor controller 42 in the present embodiment is provided with an observer model (abbreviated as "OM" in FIG. 1) 48 as a physical model which simulates the motor 36, the torque shaft 33 and the mechanical coupling section 31, i.e. the electric bending drive section 39.

Furthermore, the motor controller 42 is provided with an estimating section 49 that estimates the rotation state (rotational position, rotational velocity) of the distal end portion 33b of the torque shaft 33 based on rotation information of the motor 36 in the rotating state thereof by the motor encoder 46 and the observer model 48 as the physical model representing the rotation state of the distal end portion 33b in response to a rotation input to the proximal end portion 33a of the torque shaft 33. It is noted that an estimated value of the rotational position of the distal end portion 33b of the torque shaft 33 is also an estimated value of a rotational position of the mechanical coupling section 31.

Figure 2:
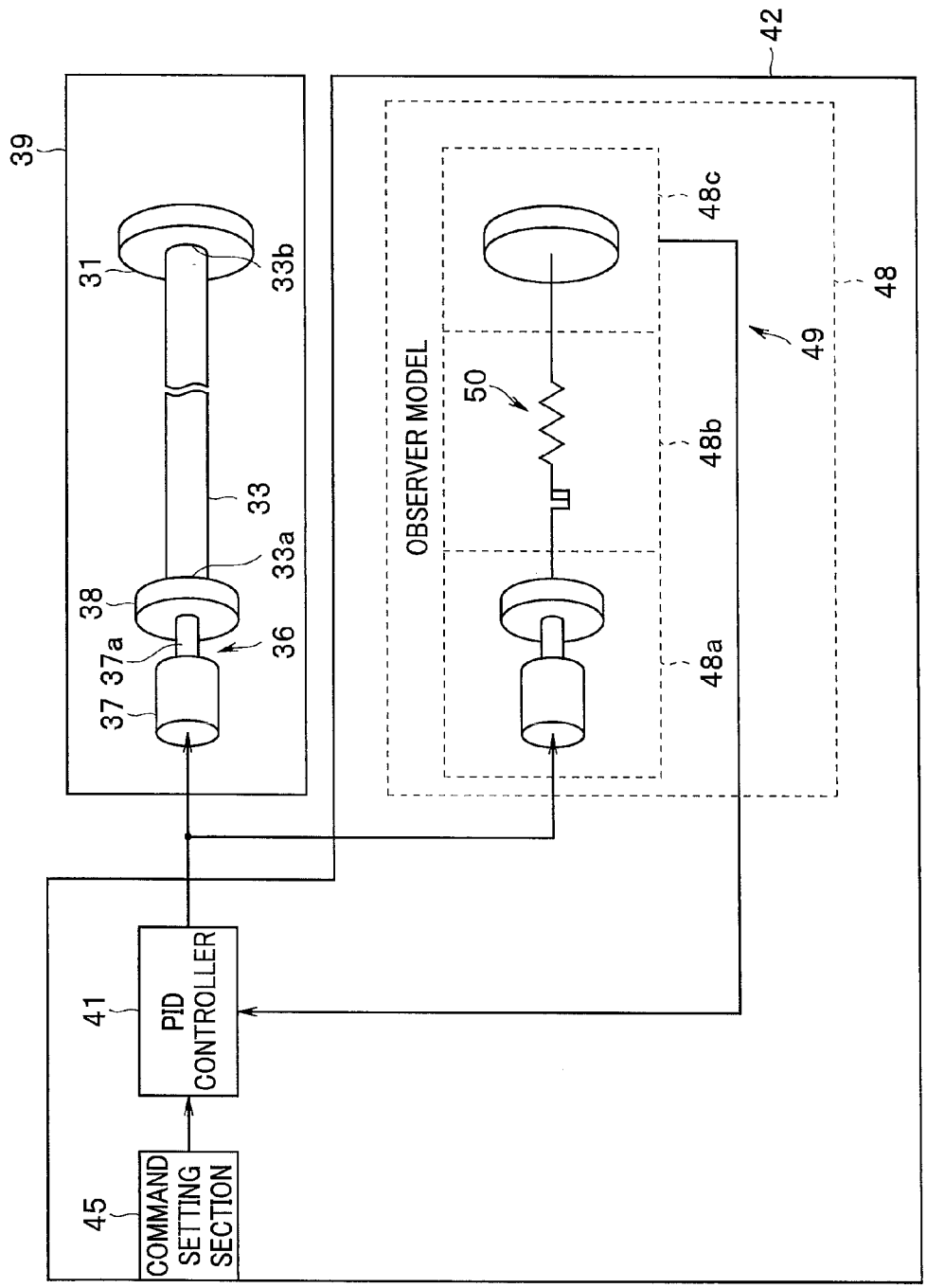
FIG. 2 is a diagram showing configuration parts of an electric bending drive section and a motor controller having an observer model as a physical model of the electric bending drive section.

FIG. 2 shows a configuration of the motor controller 42 and the electric bending drive section 39 in FIG. 1. As shown in FIG. 2, in the present embodiment, the driving command value of the PID controller 41 of the motor controller 42 is inputted to the motor 36 of the electric bending drive section 39 as a real system and to the observer model 48 as the physical model which electrically simulates the real system.

Further, in the present embodiment, the torque shaft 33 is simulated basically by a spring 50 including a friction element, as shown in FIG. 2.

As shown in FIG. 2, the rotation command value of the command setting section 45 is inputted to the PID controller 41, and the PID controller 41 outputs the driving command value corresponding to the rotation command value to the motor 36 of the electric bending drive section 39 and to a motor physical model 48a in the observer model 48 as the physical model of the electric bending drive section 39.

The observer model 48 is configured by the motor physical model 48a which simulates the motor 36, a torque shaft physical model 48b which simulates the torque shaft 33, and a mechanical coupling section physical model 48c which simulates the mechanical coupling section 31. Besides, the estimating section 49 in FIG. 1 is formed by the torque shaft physical model 48b and the mechanical coupling section physical model 48c, but actually the motor physical model 48a, the torque shaft physical model 48b and the mechanical coupling section physical model 48c are in combination as being partially entered each other, and therefore the estimating section 49 may be regarded to be configured by the motor physical model 48a, the torque shaft physical model 48b and the mechanical coupling section physical model 48c.

Figure 3:
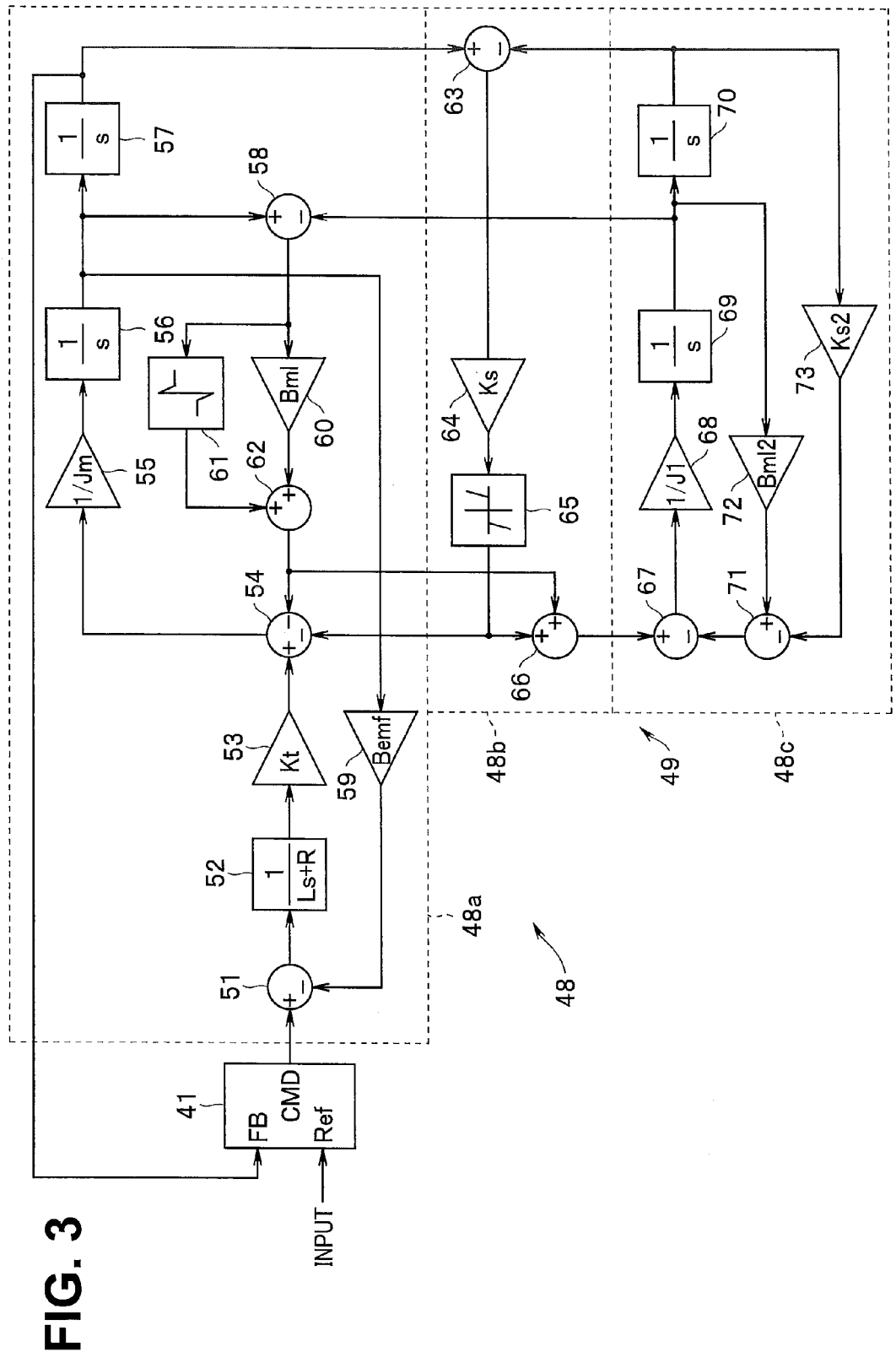
FIG. 3 is a block diagram showing a detailed configuration of the observer model in FIG. 2.

FIG. 3 shows details of the observer model 48. It is noted that the observer model 48 is shown with the estimating section 49 incorporated therein in FIG. 3. In other words, FIG. 3 shows a block configuration including the observer model 48 and the estimating section 49.

The rotation command value from the command setting section 45 is inputted to the reference input terminal Ref of the PID controller 41, and the driving command value (voltage value) is outputted from a command output terminal CMD to a block 51 of sum (adder/subtractor) which constitutes the motor physical model. The block 51 of sum adds an input signal indicated by + (plus) and subtracts an input signal indicated by − (minus) and outputs the result.

The block 51 subtracts an output value obtained by multiplication by an induced voltage constant in a block 59 of an induced voltage constant (Bemf) by the motor main body 37 from the inputted voltage value, and outputs the result to a block 52 representing an electric characteristic of the motor 36. The block 52 performs an operation of 1/(Ls+R), where s is a Laplace operator, with respect to the inputted voltage value to be converted into a current value and outputs the result to a block 53 which performs multiplication by a gain of a torque constant Kt of the motor 36. It is noted that L and R represent an inductance component and a resistance component, respectively, when the motor main body 37 is driven.

The block 53 converts the inputted current value into a torque value of the motor 36 and outputs the result to a block 54 of sum. The block 54 subtracts an output value of a block 62 of sum and an output value of a block 65, which constitutes the torque shaft physical model 48*b* and performs an operation of a dead band, from an output value of the block 53, and outputs the result to a block 55. A characteristic of the dead band in the block 65 is set to be a characteristic value which appropriately reflects the torque shaft 33 to correspond to the torque shaft 33 actually used.

The block 55 performs an operation of dividing an output value of the block 54 by an inertial moment Jm of the motor 36, and through a block 56 which performs an integral operation indicated by 1/s with respect to an output of the block 55, an operation of calculating a virtual rotational velocity of the motor is performed.

An output value of the block 56 is supplied to a block 57 for performing an operation to obtain a virtual rotational position of the motor 36, a block 58 of sum, and the block 59. Information of the rotational position outputted from the block 57 is estimated information of the virtual rotational position of the motor 36, and outputted to a feedback input terminal FB of the PID controller 41 and to a block 63 of sum which constitutes the torque shaft physical model 48*b*.

The block 58 of sum outputs a value obtained by subtracting an output value of a block 69 from the output value of the block 56 to a block 60 which performs an operation using a viscosity constant Bml of the motor 36 and to a block 61 which performs an operation by a friction constant. The block 62 of sum adds up output values of the blocks 60 and 61 and outputs the result to the block 54 of sum and a block 66 of sum.

In the torque shaft physical model 48*b*, the block 63 of sum outputs a value obtained by subtracting virtual position information of the mechanical coupling section 31, as an output value of a block 70 which constitutes the mechanical coupling section physical model 48*c*, from the information of the rotational position of the block 57 to a block 64 which performs an operation of multiplying a gain of a spring constant Ks corresponding to a dynamic characteristic (or representing a dynamic characteristic) of the torque shaft 33.

Then, an output value of the block 64 is further outputted to the block 66 of sum and the block 54 via the block 65 which performs the operation of the dead band of the torque shaft 33. The block 66 of sum outputs a value obtained by adding the output vale of the block 65 and the output value of the block 62 to a block 67 of sum which constitutes the mechanical coupling section physical model 48*c*.

In the mechanical coupling section physical model 48*c*, the block 67 outputs a value obtained by subtracting a summed output value of a block 71 of sum from the output value of the block 66, to a block 68 which performs an operation of division by an inertial moment J1 of the mechanical coupling section 31.

An output value of the block 68 is further fed to the block 69 which performs an integral operation of 1/s, and through the block 69 a virtual rotational velocity of the mechanical coupling section 31 is estimated. An output value of the block 69 is outputted to the above-mentioned block 58 and the block 70 which performs the integral operation of 1/s and a block 72 which performs an operation of a viscosity constant Bml2 of the mechanical coupling section 31.

The block 70 which performs the integral operation of 1/s with respect to the output value of the block 69 estimates a virtual rotational position of the mechanical coupling section 31 and outputs the estimated value (or the virtual value) to the block 63 and to a block 73 which performs an operation of a spring constant Ks2 of the mechanical coupling section 31.

Further, the block 71 of sum to which the output value of the block 72 is inputted sums up the output value of the block 72 and the output value of the block 73 and outputs the result to the block 67. Besides, the blocks from the block of sum denoted by the reference sign 51 to the block 73 in FIG. 3 may be implemented by software processing by a central processing unit (abbreviated as "CPU") according to a program, or the respective blocks shown in FIG. 3 may be implemented by a hardware configuration using an FPGA (Field Programmable Gate Array) or the like and electric circuit elements. Similarly, also in FIGS. 5, 6, 7 and 10, etc. as described later, configurations may be implemented by software or hardware. Further, the configurations shown in FIG. 3, etc., may be simplified by omitting a part of the blocks. Specifically, for example, it may be configured such that one of the blocks 60 and 61, e.g. the block 61 may be omitted. In this case, the block 62 which is an adder can be also omitted. The simplified configuration is described with respect to an example of the block 60 and the block 61. However, one or more other blocks may be omitted.

The observer model 48 of FIG. 3 is configured such that, in the physical model including an element in which information of the rotational velocity of the motor 36 (specifically, the output value of the block 56) is subtracted from information of the rotational velocity of the mechanical coupling section 31 (specifically, the output value of the block 69), and an element in which information of the rotational position of the mechanical coupling section 31 (specifically, the output value of the block 70) is subtracted from estimated information of the rotational position of the motor 36 (specifically, the output value of the block 57), the block 57 calculates information of the virtual rotational position of the motor 36 as the estimated information. That is, the block 57 which constitutes the physical model of the motor 36 and also constitutes the estimating section 49 calculates the information of the virtual rotational position of the motor 36 as the estimated information.

Further, the estimating section 49 feeds back the estimated information of the virtual rotational position of the motor 36 to the PID controller 41 so that the rotation of the motor 36 as the driving section is controlled to match with rotation command value inputted into the reference input terminal Ref.

Specifically, using the physical model of the torque shaft 33 and the physical model of the mechanical coupling section 31 in addition to the physical model of the motor 36, it is configured such that rotation delay of the distal end portion 33*b* of the torque shaft 33 with respect to the proximal end portion 33*b* of the torque shaft 33 is reflected on the information of the virtual rotational position in the physical model of the motor 36. That is, it is configured that the estimated information of the virtual rotational position of the motor 36 as the output value of the block 57 becomes the estimated information which reflects the rotation delay of the distal end portion 33b with respect to the proximal end portion 33b of the torque shaft 33 when the delay occurs, and the rotation delay can be improved by performing the PID control by feeding back the estimated information.

Thus, the electric endoscope 2 of the present embodiment comprises: the mechanical coupling section 31 as a drive object to be driven, the motor 36 (or the motor main body 37) constituting the driving section that generates the rotational driving force for rotationally driving the drive object, the torque shaft 33, as the transmission member having flexibility, that has a proximal end portion connected to the driving section and a distal end portion connected to the drive object, rotates around the drive shaft and transmits the rotational driving force from the driving section to the drive object, the joystick 43 as the input section for inputting the command value which instructs the target rotation amount of the driving section, the motor encoder 46 as the detecting section for detecting the rotation information of the driving section in the rotation state thereof, the estimating section 49 that estimates the rotation state of the driving section in the physical model which reflects the rotation state of the distal end portion based on the rotation information and the observer model 48 as the physical model which represents the rotation state of the distal end portion with respect to the rotation input to the proximal end portion, and the motor controller 42 as the control section that controls the driving section so that the rotation state of the distal end portion matches with a rotation state of the target rotation amount based on the rotation state of the driving section in the physical model estimated by the estimating section 49.

Next, the operation of the present embodiment will be described. As shown in FIG. 1, the electric endoscope 2 is connected to the signal processing apparatus 4 and a surgeon grasps the operation portion 12 and inserts the insertion portion 11 into a bent body cavity of the subject 9. When inserting a distal end side of the insertion portion 11 into a deeper side of the body cavity, the surgeon performs the tilting operation of the joystick 43 in accordance with bending in the body cavity.

In the present embodiment, since it is configured that the motor 36 is arranged not in the operation portion 12 but in the connector 3 and the mechanical coupling section 31 arranged in the operation portion 12 is driven through the torque shaft 33, the surgeon can perform an instruction operation for bending with good operability without bearing a heavy weight (due to the motor 36) when the surgeon grasps the operation portion 12.

However, since the rotational driving force of the motor 36 is transmitted by the torque shaft 33 inserted into the universal cable 13, there is a case where a magnitude of a disturbance load on the torque shaft 33 varies, as described below.

Figure 4:
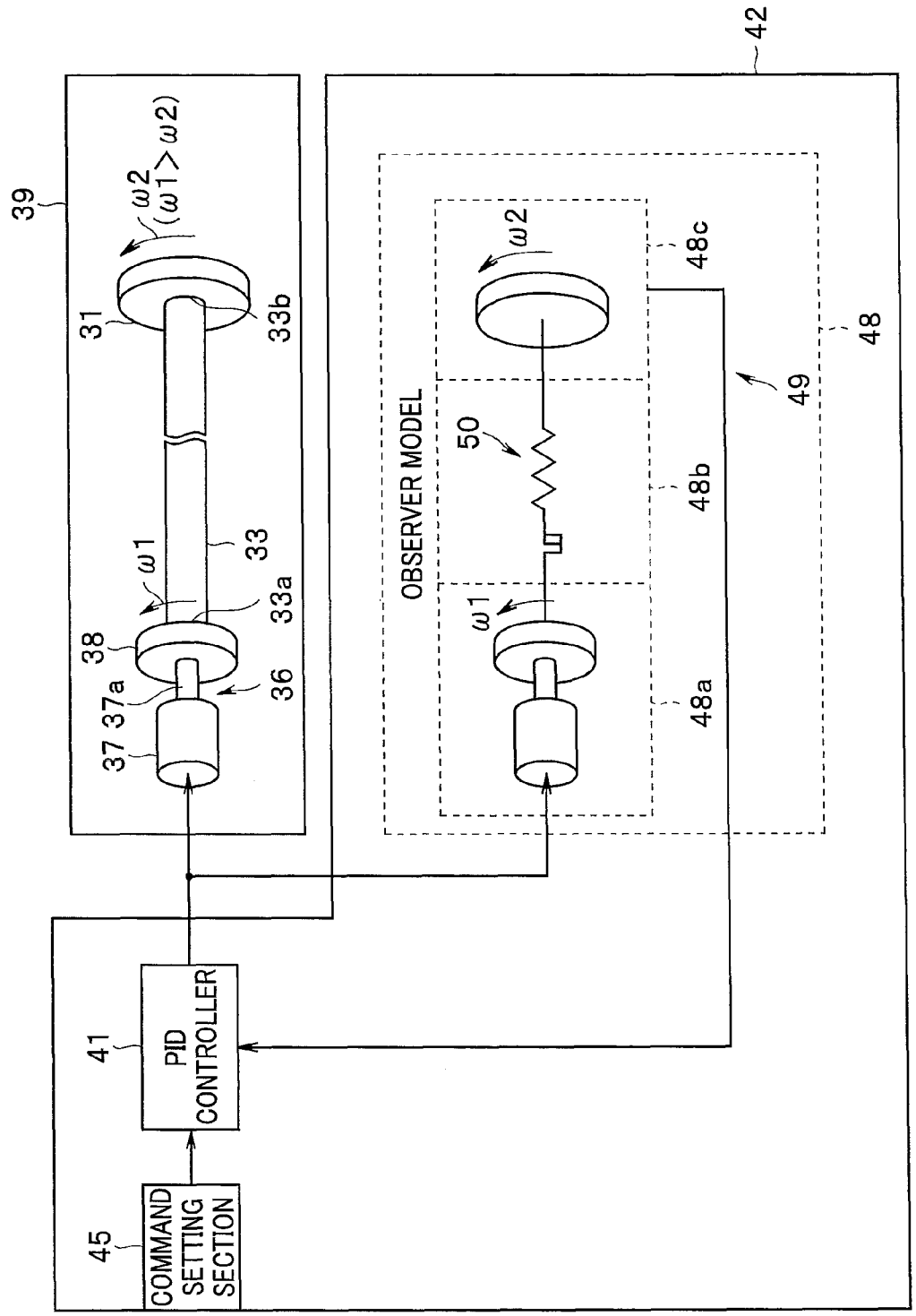
FIG. 4 is an explanatory diagram showing a state in which a rotational velocity of a torque shaft cannot follow a rotational velocity of a motor by a shape change of the torque shaft.

FIG. 4 shows an explanatory diagram of a state in which a shape change of the torque shaft 33 occurs with a shape change of the universal cable 13, so that the disturbance load on the torque shaft 33 varies. When the motor 36 rotates at rotational velocity ω1, for example, in a state of the universal cable 13 being relatively straight, for example, the mechanical coupling section 31 also rotates at the rotational velocity ω1.

However, when the user such as the surgeon changes an insertion length of the insertion portion 11 into the body cavity in a state where the user grasps the operation portion 12, there is a case in which a proximal end side of the universal cable 13 moves to be brought into a greatly bent state from the relatively straight state.

In the case where the universal cable 13 is brought into the greatly bent state, as mentioned above, there arises a case in which the rotational velocity is lowered to a rotational velocity ω2 smaller than the rotational velocity ω1 from the state of the mechanical coupling section 31 rotating at the rotational velocity ω1.

In the present embodiment, as shown in FIG. 2, FIG. 3 (and FIG. 4), the motor physical model 48a, the torque shaft physical model 48b and the mechanical coupling physical model 48c which simulate the motor 36, torque shaft 33 and the mechanical coupling section 31, respectively are provided. Further, as shown in FIG. 3, the distal end position of the torque shaft 33, in other words, the estimated value of the virtual rotational position of the mechanical coupling section 31 (the output value of the block 70), is calculated from the torque shaft physical model 48b, and using the estimated value of the virtual rotational position and the estimated value of the virtual rotational velocity of the mechanical coupling section 31 (the output value of the block 69), the position information for correcting the command value of the motor 36 (the output value of the block 57) is fed back to the PID controller 41.

Therefore, according to the present embodiment, it is possible to rotationally drive the motor 36 so as to reduce the rotation delay at the distal end portion 33b of the torque shaft 33 or at the mechanical coupling section 31 (with respect to the proximal end portion 33a of the torque shaft 33) without providing a sensor at the distal end portion 33b of the torque shaft 33 or at the mechanical coupling section 31. Further, since the motor 36 is provided at the connector 3, for example, which is other than the operation section 12 of which weight becomes a load for the user when the user grasps the operation section, good operability can be secured.

Figure 11:
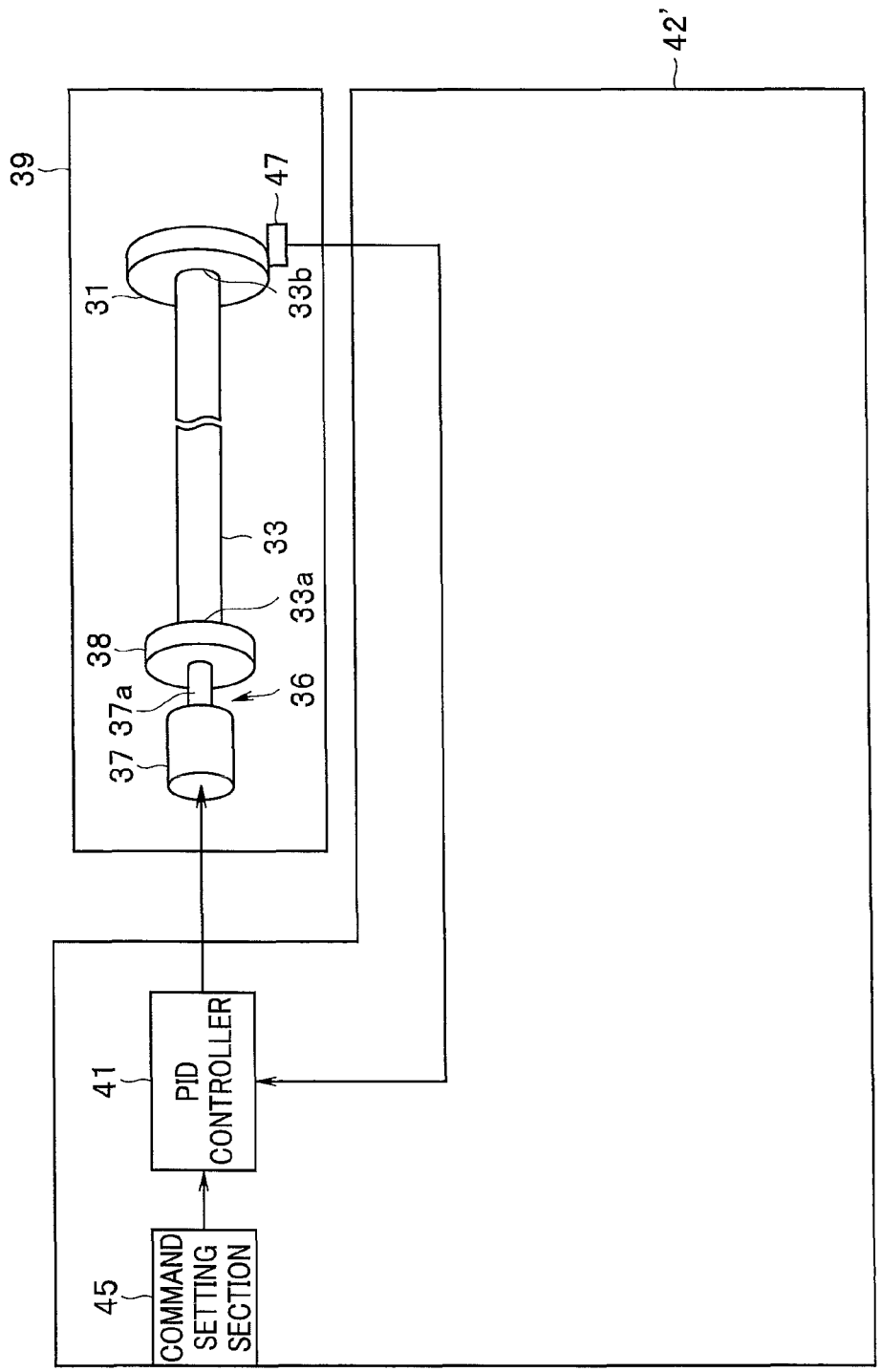
FIG. 11 is a diagram showing a configuration in which a sensor for detecting a rotational position of a mechanical coupling section is provided at the mechanical coupling section in the configuration of FIG. 2 and PID control is performed by feeding back the rotational position.

Besides, in the present embodiment, a sensor for detecting the rotational position, the rotational velocity, etc. of the mechanical coupling section 31 is not provided at the mechanical coupling section 31, but it may be configured, as shown in FIG. 11, such that a sensor 47 for detecting the rotational position, etc. of the mechanical coupling section 31 is provided and a detection value of the sensor 47 is fed back to be inputted into the PID controller 41, and the PID controller 41 performs the PID control of the motor 36 to reduce the rotation delay by the detection value of the sensor 47. In this case, the motor controller 42' does not include the observer model 48.

Next, a first modified example of the present embodiment will be described. In the torque shaft 33 which is used as the transmission member for transmitting the rotational driving force, the closely wound coil 33d is used in the longitudinal direction of the shaft as the driving axis (as shown in FIG. 1). Therefore, there is a case in which a difference occurs in a transmission characteristic in dependence on a case of rotation of the motor 36 in a forward direction and a case of rotation of the motor 36 in a reverse direction.

Therefore, in the present modified example, in order to make better response by reducing the rotation delay of the mechanical coupling section 31 with respect to an operation command for bending in the case of performing rotational drive in any of the directions, it is configured that two parameters are prepared in accordance with dynamic characteristics in the two rotational directions and the parameter is selectively used in accordance with the rotational direction.

Figure 5:
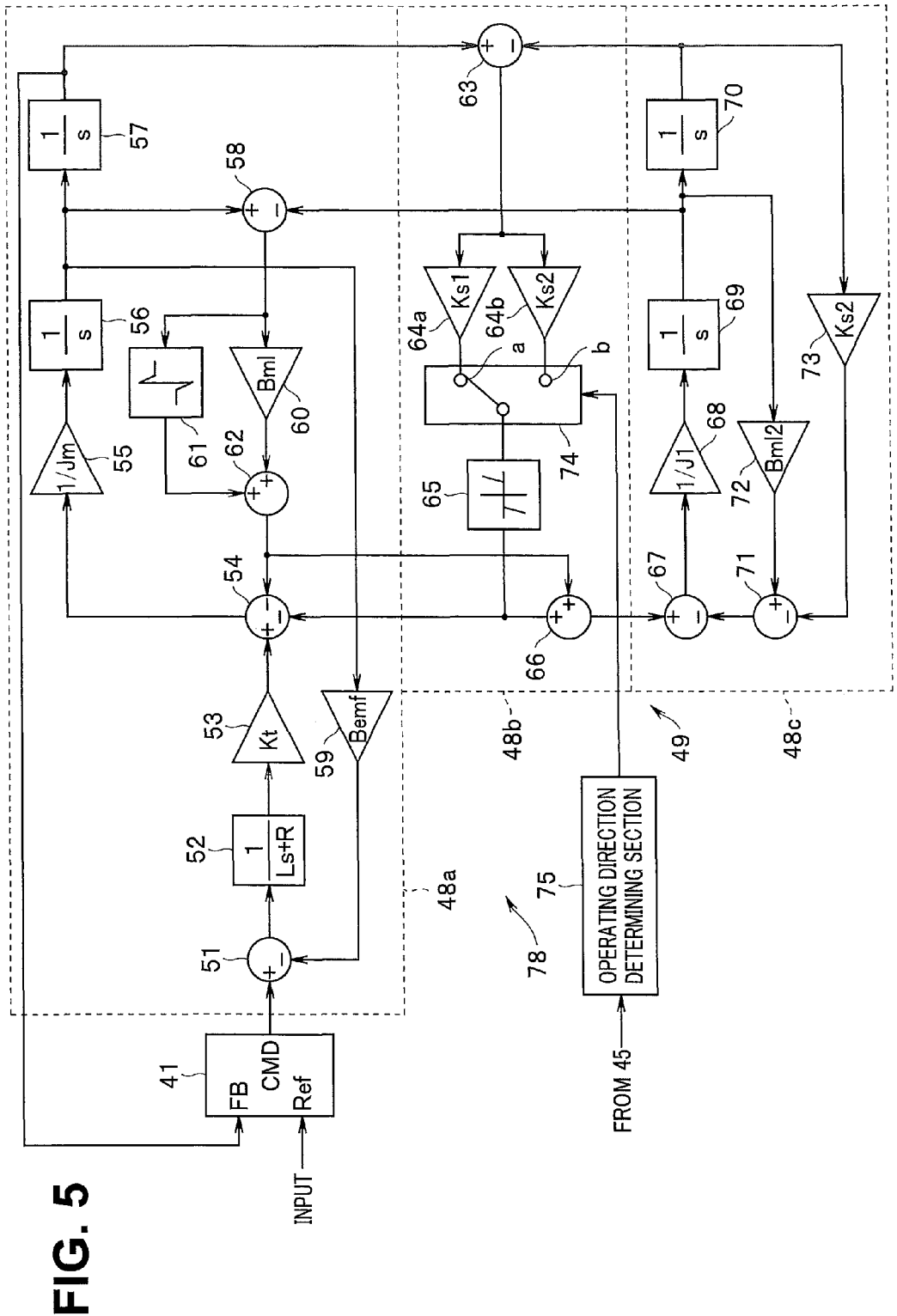
FIG. 5 is a block diagram showing an observer model in a first modified example of the first embodiment.

FIG. 5 shows an observer model 78 in the present modified example.

The observer model 78 has modification that the configuration of the torque shaft physical model 48b (which constitute the estimating section 49) in the observer model 48 shown in FIG. 3 is partially modified.

The output of the block of sum 63 is supplied to the block 65 through a block 64a of a gain of a first spring constant Ks1 (as a first parameter) or a block 64b of a gain of a second spring constant Ks2 (as a second parameter), the first and second constants being set to correspond to a first rotational direction of the torque shaft 33 around the longitudinal direction thereof and a second rotational direction which is a reverse direction of the first rotational direction, respectively, and through a changeover switch 74. Further, the present modified example is provided with an operating direction determining section 75 which determines in which direction of the first rotational direction and the second rotational direction the operation is performed. The operating direction determining section 75 has a function of a rotational direction detecting section that detects the rotational direction of the torque shaft 33 as the transmission member.

Further, the changeover switch 74 is switched such that a contact a becomes on when the operating direction is the first rotational direction according to the determination of the operating direction by the operating direction determining section 75, and a contact b becomes on when the operating direction is the second rotational direction.

In other words, the estimating section 49 including the torque shaft physical model 48b selects the first parameter or the second parameter in accordance with the rotational direction of the torque shaft 33 based on the rotational direction of the torque shaft 33 determined by the operating direction determining section 75, and estimates the rotation state of the distal end portion 33b of the torque shaft 33.

It is noted that the operating direction determining section 75 determines a present rotational direction (operating direction) of the torque shaft 33 from the output value of the command setting section 45, for example. The other configurations are the same as those of the first embodiment.

The present modified example has the operational effects of the first embodiment, and further according to the present modified example, when the rotational direction changes, the mechanical coupling section 31 can be also rotationally driven with a good response characteristic in response to the change of the rotational direction. Therefore, according to the present modified example, it is possible to perform bending drive of the bending portion 16 while securing the good operability. Besides, the user tilts the stick of the joystick 43 in a direction corresponding to a bending direction so as to bend the bending portion 16 in a desired bending direction, and a detection value of the potentiometer 43a increases or decreases corresponding to the tilting direction. Further, the rotational direction of the rotating shaft 34a of the motor 36 is reversed in dependence on the case where the detection value increases and the case where the detection value decreases. Therefore, it can be said that the joystick 43, which forms a bending instruction operation section (or bending instruction operation means) for instructing the bending command value, forms a rotational-direction-instruction operation section (or rotational-direction-instruction operation means) that performs an instruction operation for the rotational drive in the first rotational direction or the second rotational direction which is reverse to the first rotational direction.

Figure 6:
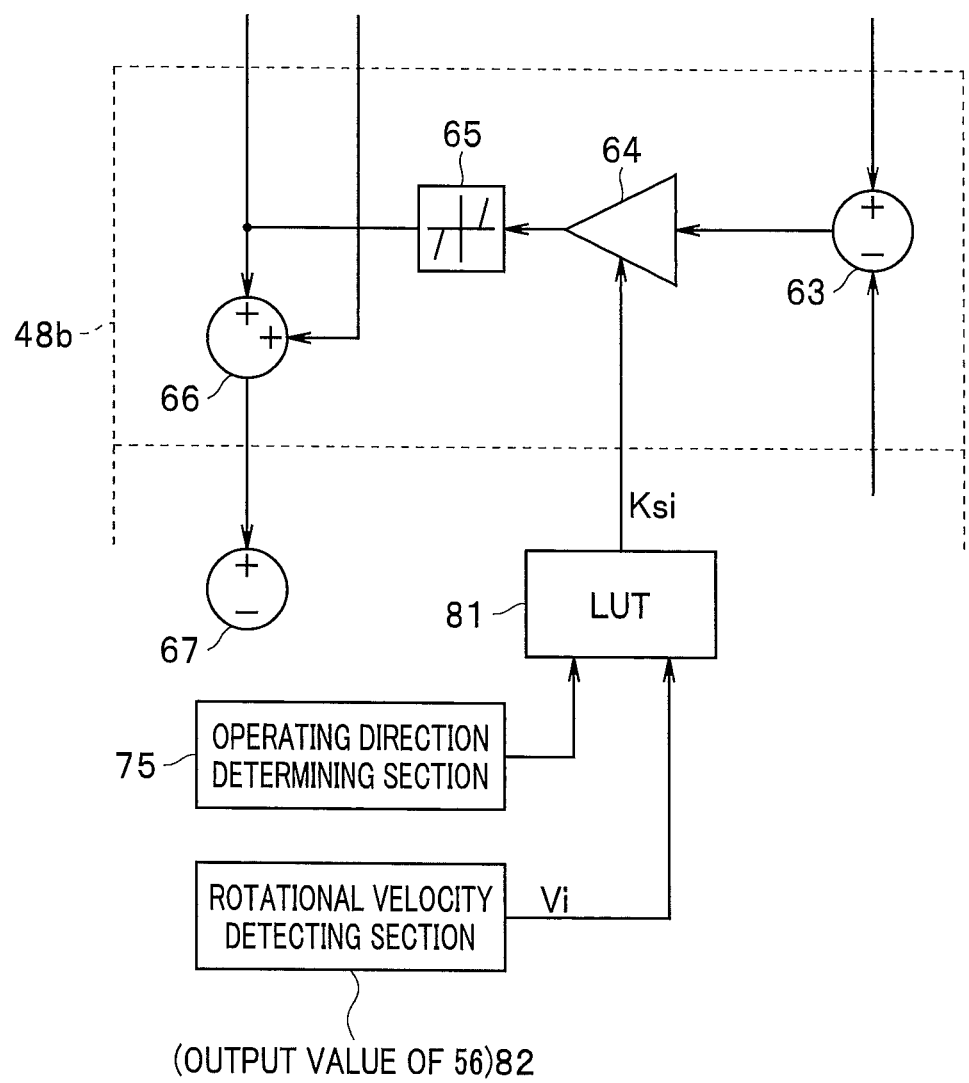
FIG. 6 is a block diagram showing an observer model in a second modified example of the first embodiment.

FIG. 6 shows a configuration of peripheral part of the torque shaft physical model 48b in a second modified example.

In the first modified example, the spring constant which simulates the torque shaft 33 is switched in accordance with the operating direction.

Even in a state where the operating direction is not changed, that is, in a state of rotation in a certain direction, there is a possibility that the transmission characteristic varies in dependence on a case where the rotational velocity is changed at a large rotational velocity and a case where the rotational velocity is changed at a small rotational velocity.

In the present modified example, in order to reflect the dynamic characteristic of the torque shaft 33 with higher fidelity, it is controlled such information of the operating direction and information of the rotational velocity in the operating direction are inputted in a lookup table (abbreviated as "LUT") 81 and corresponding spring constant Ksi is read out according to the two pieces of input information and the block 64 performs the operation using the read spring constant Ksi. It is noted that the block 64 performs the operation using the spring constant Ksi inputted from the LUT 81.

In the LUT 81, spring constants Ksi of the torque shaft 33, which are measured in the two operating directions at a plurality of typical rotational velocities Vi in advance, are stored to be associated with the two pieces of input information. It is noted that, when the rotational velocity Vi changes by a value less than a threshold (in a state where the rotational direction is not changed), the same value of Ksi is read, and when the rotational velocity Vi changes by a value not less than the threshold, a value of the spring constant Ksi different from the value of Ksi for Vi is read.

Then, in actually operating the electric bending drive section 39, the information of the operating direction by the operating direction determining section 75 and the information of a rotational velocity detecting section 82 which detects the rotational velocity of the torque shaft 33 are inputted to the LUT 81 and the corresponding spring constant Ksi is set to the block 64.

Besides, as the rotational velocity detecting section 82, the information of the rotational velocity of the motor 36, which is calculated from the information of the rotational position (rotational angle) of the motor 36 or the motor main body 37, detected by the motor encoder 46, is used.

The other configurations are the same as those of the first embodiment. The present modified example has the same operational effects as those of the first embodiment, and further according to the present modified example, it is possible to rotationally drive the mechanical coupling section 31 with better response characteristic when the rotational direction is change or the rotational velocity is changed and thus perform the bending drive of the bending portion 16 securing good operability.

Besides, in the present modified example, instead of inputting the information of the rotational velocity detecting section 82 into the LUT 81, it may be configured to use the output value of the block 56, i.e. the estimated value of the rotational velocity of the motor 36.

Next, a third modified example of the first embodiment will be described. As described in the first embodiment, since the torque shaft 33 is inserted through the universal cable 13, when the universal cable 13 is bent, more disturbance load is exerted on the motor 36 (or motor main body 37) in comparison with a state where the universal cable is not bent.

The present modified example performs variable control of a gain of the PID controller 41 in accordance with the disturbance torque so that the electric bending drive can be performed with better precision. In other words, by performing gain scheduling for variable control of the gain (parameter) of the PID controller 41 in accordance with the disturbance torque, it is configured such that the electric bending drive can be performed with better precision when the disturbance torque varies.

Figure 7:
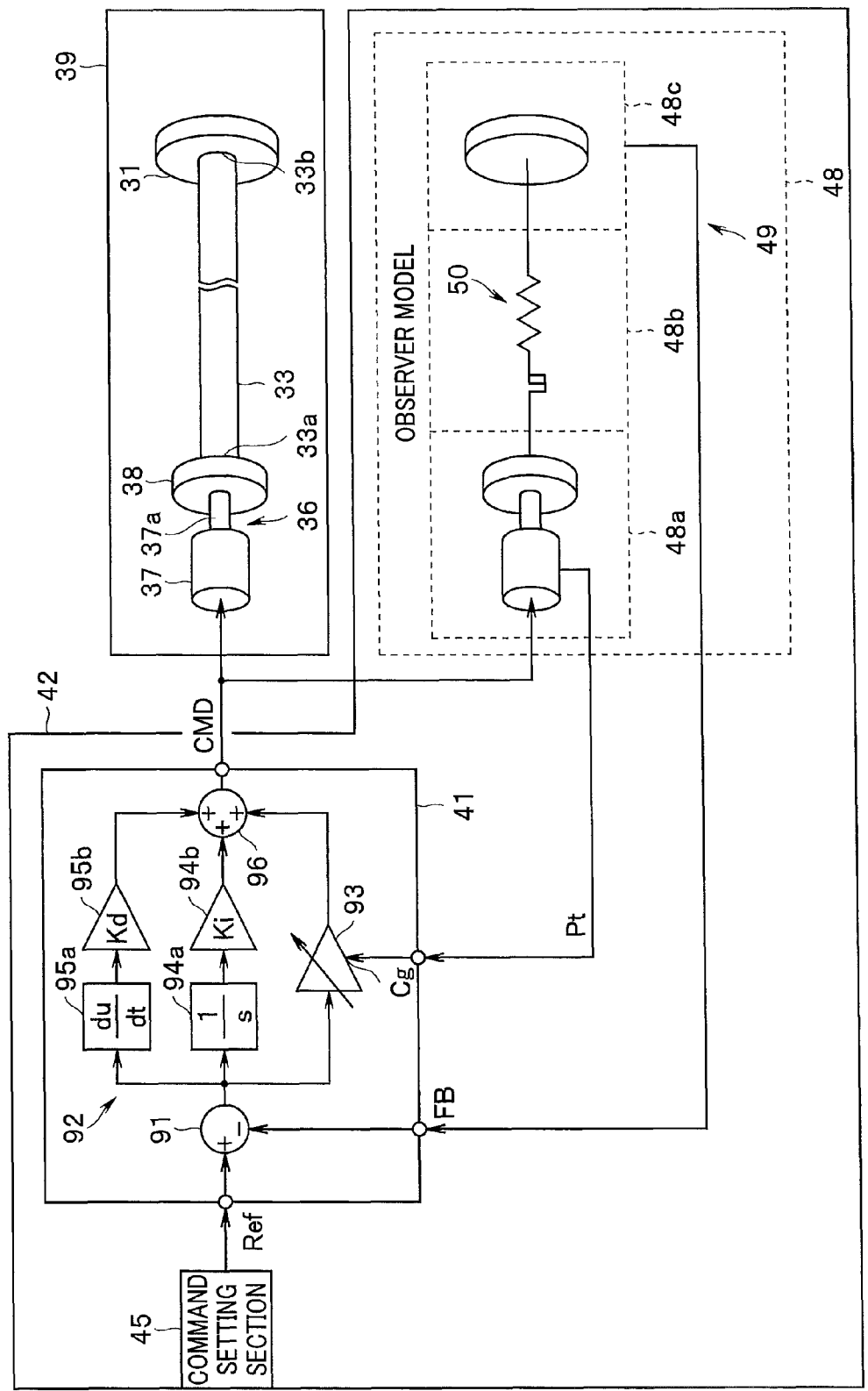
FIG. 7 is a diagram showing configuration parts of the electric bending drive section and a motor controller having an observer model in a third modified example of the first embodiment.

FIG. 7 shows a configuration of the electric bending drive section 39 and the motor controller 42 in a third modified example. As shown in FIG. 7, the command value from the command setting section 45 and the position information from the observer model 48 are inputted to a block 91 of sum of the PID controller 41 and the block 91 subtracts the latter from the former and outputs the result to the PID controller main body 92.

The PID controller main body 92 includes the block 93 of the variable gain that performs proportional control, a block 94a of an integral operation of 1/s that performs integral control and a block 94b of a gain Ki provided in series with the block 94a, and a block 95a of a time-differential operation that performs differential control and a block 95a of a gain Kd provided in series with the block 95a. These three output values are added up by a block 96 of sum and the result is outputted to the motor 36 of the electric bending drive section 39 and the observer model 48 from the output terminal CMD.

According to the present modified example, in the configuration of the first embodiment, etc. for example, the motor-torque estimated value Pt as an estimated value of the disturbance torque in the observer model 48 is applied to a gain control terminal Cg of the block 93 of the variable gain, to control a gain Gp of the block 93.

Figure 10:
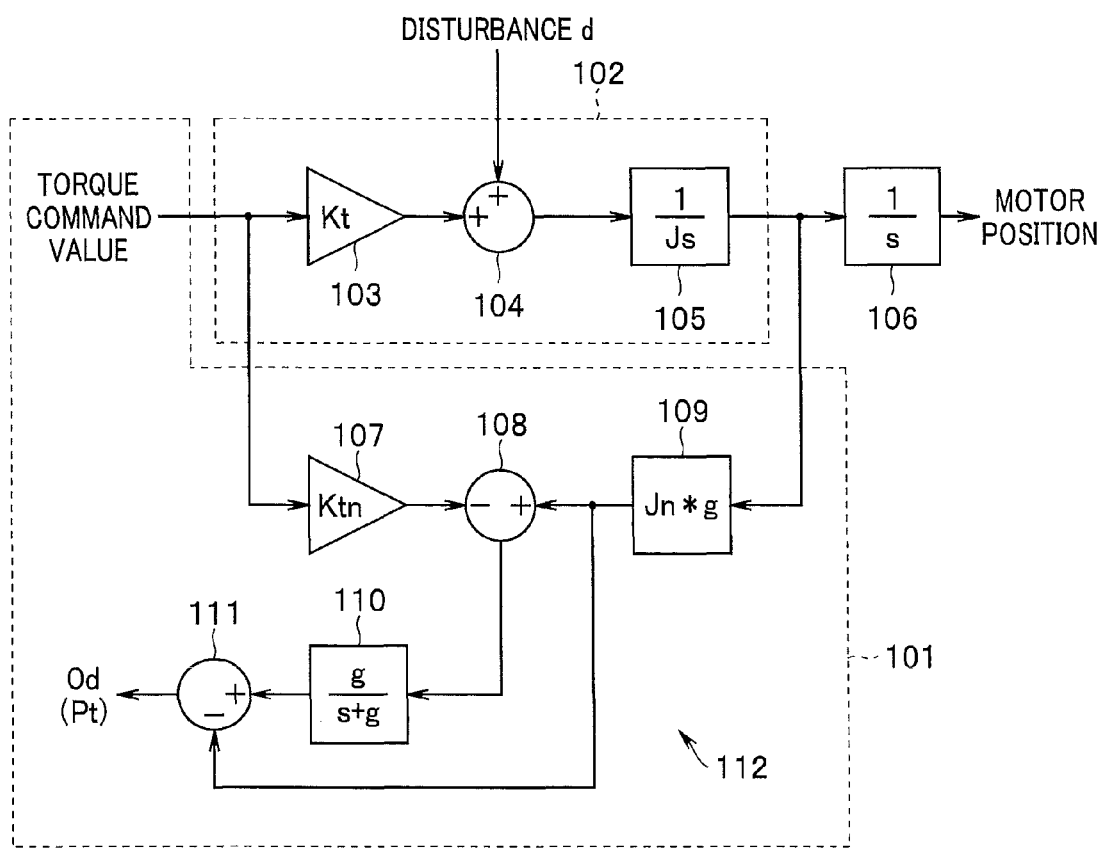
FIG. 10 is a block diagram showing a configuration of peripheries of a disturbance torque observer model in a fourth modified example of the first embodiment.

As the motor-torque estimated value Pt, the output value of the block 53 in FIG. 3 and FIG. 5, for example, may be used. Further, as shown in FIG. 10 as described later, an estimated value by a disturbance torque observer model may be used.

Figure 8:
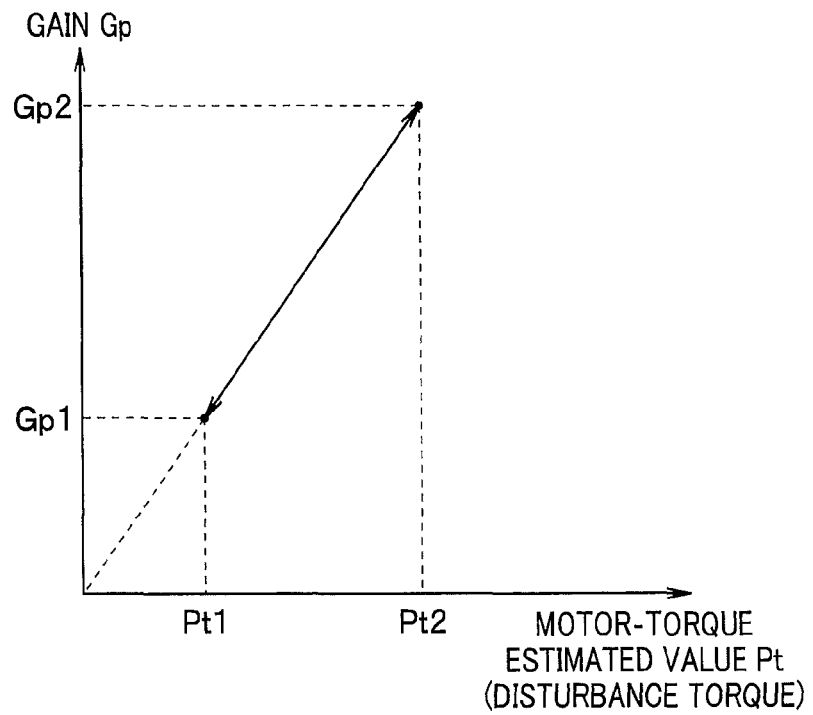
FIG. 8 is a diagram showing a characteristic example of varying a value of a gain of proportional control in accordance with an estimated value of a motor torque.

FIG. 8 shows gain scheduling for controlling a magnitude of the variable gain for the proportional control, in accordance with a magnitude of the motor-torque estimated value Pt. As shown in FIG. 8, the gain Gp of the block 93 is variably set in proportion to a value of the motor-torque estimated value Pt.

For example, the gain becomes Gp1 at a value Pt1 which is the smallest value of the motor-torque estimated value Pt, the gain Gp increases in proportion to an increase of the motor-torque estimated value Pt, and the gain becomes Gp2 at a value Pt2 which is the largest value of the motor-torque estimated value Pt.

Figure 9:
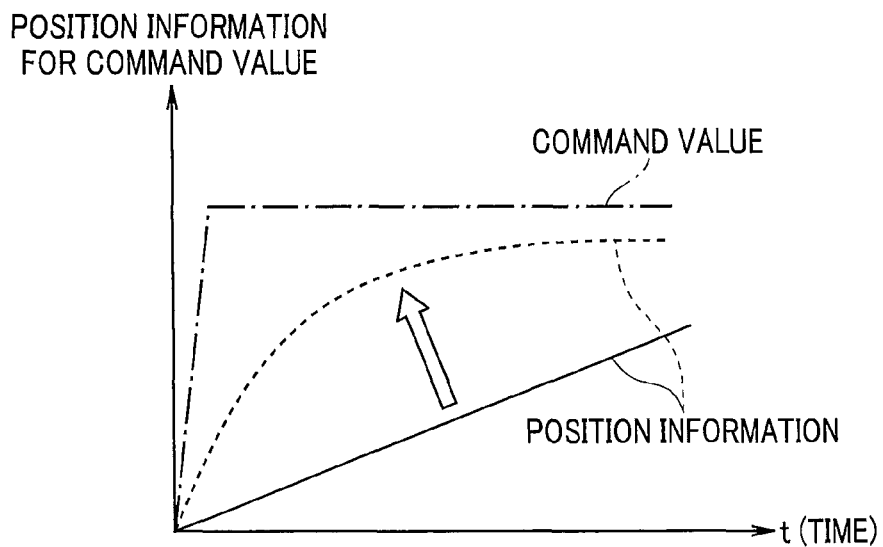
FIG. 9 is an explanatory diagram for improving a response characteristic for a command value by gain scheduling.

For example, when the above gain Gp is fixed, the position information to be used in the PID control for the command value can secure a good response characteristic, as shown by the dotted line in FIG. 9, when the disturbance torque is small. However, when the disturbance torque becomes larger, the position information to be used in the PID control has a large time delay as shown by the solid line. It is noted that the command value is shown by the dashed line in FIG. 9.

Therefore, in the present modified example, when the motor-torque estimated value Pt increases, the gain Gp is set to be larger in accordance with the increase, so that the position information by gain scheduling can be generated so as to enable the PID control in which a good response is secured even in a case where the motor-torque estimated value Pt increases as in a case where the motor-torque estimated value Pt is small.

The present modified example improves the response characteristic even in a case where the disturbance torque varies, as shown by the void arrow in FIG. 9.

As in a fourth modified example of the present embodiment, it may be configured that the motor-torque estimated value Pt is calculated using a disturbance torque observer model 101 which forms a first physical model part and a block 102 which forms a second physical model part, as an observer model of the motor 36 (as the driving section).

In FIG. 10, the command value of the torque is inputted into a block 103 of a gain of a (motor) torque constant Kt which constitutes the block 102 of an equivalent model of the motor 36, and into a block 107 of a gain of a design motor torque constant Ktn which constitutes the disturbance torque observer model 101. The block 107 calculates an output torque of the rotating shaft of the motor 36 for the command value.

An output value of the above block 103 is added to a disturbance d, when the disturbance d as a load is exerted on the rotating shaft of the motor 36, and through a block 105 which performs integration of 1/Js using a motor inertial moment J, information of the rotational velocity is generated. It is noted that the disturbance d as the load on the rotating shaft is also exerted on the driving axis of the torque shaft 33, to which the rotating shaft is connected, as a load. The information of the rotational velocity provides the position information of the motor 36 through a block 106 which performs integration of 1/s, and is outputted to a block 108 of sum as an estimated torque value exerted on the rotating shaft of the motor 36 through a block 109 which constitutes the disturbance torque observer model 101 and multiplies a design torque constant Jn and a pole g of the observer.

The disturbance torque observer model 101 includes a disturbance calculating section 112 that calculates a disturbance-torque estimated value Od as described below. In summary, the disturbance-torque estimated value Od as a disturbance torque as a load on the rotating shaft of the motor 37 is calculated from a difference between an estimated torque value as an output value from the block 102 as a physical model of the motor 37 through (the block 109 of) the block 101, and an output value as an output torque outputted from the rotating shaft in response to input of the torque command value (the input of the torque command value passed) through a block 107 of a gain.

A block 108 of sum subtracts an output torque value as the output value of the block 107 from the estimated torque value as an output value of the block 109, to calculate a disturbance torque in dependence on the pole g. The disturbance torque is outputted to a block 111 of sum through a block 110 which performs a filter operation of g/(s+g).

A block 111 of sum subtracts an output value of the block 109 from an output value of the block 110 and outputs the disturbance-torque estimated value Od which corresponds to the motor-torque estimated value Pt. The disturbance torque estimated value Od is applied to the gain control terminal Cg of the block 93 of the PID controller 41.

Then, the gain scheduling of the PID controller 41 is performed by the disturbance-torque estimated value Od, so that the PID control can be performed with the good response characteristic even when the disturbance on the rotating shaft of the motor 36 varies.

The present modified example has substantially the same operational effects as those of the third modified example. It is noted that embodiments and the like obtained by partial combination or the like of the above-described embodiments or modified examples belong to the present invention. Further, the foregoing physical models are not limited to the configurations of the observer model 48, 78, etc., and may have configuration for estimating the rotation state of the driving section and the motor constituting the driving section by simplified models.

What is claimed is:

1. An electric endoscope comprising:
    a motor that generates a rotational driving force;
    a torque shaft having flexibility, for transmitting the rotational driving force, the torque shaft having a proximal end portion connected to the motor;
    a mechanical connecting section for bending a bending portion by the rotational driving force transmitted through the torque shaft, the mechanical connecting section being connected to a distal end portion of the torque shaft;
    an input section that inputs a bending command value for instructing bending of the bending portion;
    a detecting section that detects a present rotational position of the motor;
    a command setting section that sets a rotation command value as a target rotation amount of the motor based on the bending command value and the rotational position;
    an estimating section that estimates a virtual rotational position of the motor such that a rotation state of the distal end portion matches with a rotation state of the target rotation amount, based on the rotation command value, a torque shaft physical model that simulates the torque shaft, and a mechanical connecting section physical model that simulates the mechanical connecting section;
    a control section that corrects the rotation command value based on a virtual rotation state of the motor and controls the motor; and
    a rotational direction detecting section that detects a rotational direction of the torque shaft,
    wherein the estimating section has a first parameter representing a dynamic characteristic in rotating the torque shaft around a driving axis of the torque shaft in one direction in the torque shaft physical model, and a second parameter representing a dynamic characteristic in rotating the torque shaft around the driving axis in other direction in the torque shaft physical model, and
    the estimating section estimates the rotation state of the distal end of the motor by selecting the first parameter or the second parameter in accordance with the rotational direction of the torque shaft based on the rotational direction detected by the rotational direction detecting section.

2. The electric endoscope according to claim 1, comprising a disturbance calculating section that calculates a disturbance torque as a load on the driving axis of the torque shaft from a difference between an estimated torque value outputted from a motor physical model that simulates the motor for an input of the bending command value from the input section, and an output torque outputted from the driving axis for the input of the bending command value,
    wherein the control section controls the motor using the disturbance torque.

3. The electric endoscope according to claim 2, wherein a gain of a PID control apparatus constituting the control section that controls the motor is variably controlled using the disturbance torque.

4. The electric endoscope according to claim 1, further comprising a rotation instruction operation section that performs a rotation instruction operation for rotating the toque shaft in the one direction, and a rotation instruction operation for rotating the toque shaft in the other direction.

5. An electric endoscope comprising:
    a motor that generates a rotational driving force;
    a torque shaft having flexibility, for transmitting the rotational driving force, the torque shaft having a proximal end portion connected to the motor;
    a mechanical connecting section for bending a bending portion by the rotational driving force transmitted through the torque shaft, the mechanical connecting section being connected to a distal end portion of the torque shaft;
    an input section that inputs a bending command value for instructing bending of the bending portion;
    a detecting section that detects a present rotational position of the motor;
    a command setting section that sets a rotation command value as a target rotation amount of the motor based on the bending command value and the rotational position;
    an estimating section that estimates a virtual rotational position of the motor such that a rotation state of the distal end portion matches with a rotation state of the target rotation amount, based on the rotation command value, a torque shaft physical model that simulates the torque shaft, and a mechanical connecting section physical model that simulates the mechanical connecting section; and
    a control section that corrects the rotation command value based on a virtual rotation state of the motor and controls the motor, wherein
    the electric endoscope further comprises a motor physical model including a first block that perform an operation of converting a voltage value, which is a driving command value to the motor, into a current value by performing an operation of $1/(Ls+R)$ and outputting a result, where s is a Laplace operator, and L and R represent inductance and resistance, respectively, of the motor, a second block that multiplies the result of the first block by a gain of a torque constant Kt of the motor, a third block that divides an output of the second block by an inertial moment Jm of the motor and outputs a result, a fourth block that performs an integral operation of $1/s$ with respect to an output of the third block, and a fifth block that performs an integral operation of $1/s$ with respect to an output of the fourth block,
    the torque shaft physical model includes a sixth block that multiplies a gain of a spring constant Ks corresponding to a dynamic characteristic of the torque shaft with respect to an output of the fifth block, and a seventh block that performs processing of an operation of a dead band, the dead band corresponding to the dynamic characteristic of the torque shaft,
    the mechanical connecting section physical model includes an eighth block that performs an operation of dividing an output of the seventh block by an inertial moment Jl of the mechanical connecting section, a ninth block that performs an integral operation of $1/s$ with respect to an output of the eighth block, and a tenth block that performs an integral operation of 1/s with respect to an output of the ninth block, and the estimating section subtracts the output of the seventh block from the output of the second block by an eleventh block and output a result to the third block, and subtracts an output of the tenth block from the output of the fifth block by an twelfth block and outputs a result to the sixth block, to thereby output an estimated value of a rotational position of the motor from the fifth block to the control section.

6. The electric endoscope according to claim 5, wherein the estimating section further subtracts the output of the ninth block from the output of the fourth block by a thirteenth block, subtracts an output obtained by performing, by a fourteenth block, an operation of a viscosity constant Bml1 of the motor with respect to an output of the thirteenth block, from the output of the second block, by the eleventh block, and outputs a result to the third block.

7. The electric endoscope according to claim 5, wherein the mechanical connecting section physical model includes a fifteenth block that performs an operation of a viscosity constant Bml2 of the mechanical connecting section with respect to the output of the ninth block and a sixteenth block that subtracts an output of the fifteenth block from the output of the seventh block and outputs a result to the eighth block.

8. An electric endoscope comprising:
a motor that generates a rotational driving force;
a torque shaft having flexibility, for transmitting the rotational driving force, the torque shaft having a proximal end portion connected to the motor;
a mechanical connecting section for bending a bending portion by the rotational driving force transmitted through the torque shaft, the mechanical connecting section being connected to a distal end portion of the torque shaft;
an input section that inputs a bending command value for instructing bending of the bending portion;
a detecting section that detects a present rotational position of the motor;
a command setting section that sets a rotation command value as a target rotation amount of the motor based on the bending command value and the rotational position;
an estimating section that estimates a virtual rotational position of the motor such that a rotation state of the distal end portion matches with a rotation state of the target rotation amount, based on the rotation command value, a torque shaft physical model that simulates the torque shaft, and a mechanical connecting section physical model that simulates the mechanical connecting section; and
a control section that corrects the rotation command value based on a virtual rotation state of the motor and controls the motor,
wherein the electric endo scope further comprises:
a rotational velocity detecting section that is provided at the motor and detects a rotational velocity of a rotating shaft to which the proximal end portion of the torque shaft is connected;
a rotational direction detecting section that detects a rotational direction around a driving axis of the torque shaft; and
a storage section that stores a first parameter and a second parameter respectively including a plurality of parameter values that indicate dynamic characteristics in the torque shaft physical model in rotating the torque shaft around the driving axis in one direction and in other direction opposite to the one direction, and reflect changes of the dynamic characteristics in the one direction and in the other direction according to the rotational velocity,
wherein the estimating section reads a parameter value of the first parameter or the second parameter corresponding to the dynamic characteristic of the torque shaft from the storage section based on the rotational direction detected by the rotational direction detecting section and information of the rotational velocity detected by the rotational velocity detecting section, and estimates the rotation state of the distal end portion using the read parameter value.

9. The electric endoscope according to claim 8, wherein the storage section stores a plurality of spring constants corresponding to the dynamic characteristics of the torque shaft as the parameter values of the first and second parameters.

* * * * *